United States Patent [19]

Chan

[11] Patent Number: 5,328,933
[45] Date of Patent: Jul. 12, 1994

[54] CYCLOPENTANE HEPTENYLNITRO AND HEPTANYLNITRO-2-ALIPHATIC OR ARYL ALIPHATIC DERIVATIVES AND HOMOLOGUES

[75] Inventor: Ming F. Chan, San Diego, Calif.

[73] Assignee: Allergan, Inc., Irvine, Calif.

[21] Appl. No.: 967,603

[22] Filed: Oct. 28, 1992

[51] Int. Cl.$^5$ .................. C07C 205/03; A01K 31/557
[52] U.S. Cl. .................................... 514/727; 568/704
[58] Field of Search .................... 568/704; 514/727

[56] References Cited

U.S. PATENT DOCUMENTS

| | | | |
|---|---|---|---|
| 4,599,353 | 7/1986 | Bito | 514/530 |
| 4,994,274 | 2/1991 | Chan et al. | 514/530 |
| 5,028,624 | 7/1991 | Chan et al. | 514/530 |
| 5,034,413 | 7/1991 | Chan et al. | 514/530 |

FOREIGN PATENT DOCUMENTS 0364417 4/1990 European Pat. Off. .

OTHER PUBLICATIONS

Starr, M. S., "Further Studies on the Effect of Prostaglandin on Intraocular Pressure in the Rabbit," Exp. Eye. Res. (1971), pp. 170–177.
Bito, L. Z., "Prostaglandins and Related Compounds as Potential Ocular Therapeutic Agents," Biological Protection with Prostaglandins, Cohen, M. ed., Boca Raton, Fla., CRC Press Inc., 1985, pp. 231–252.
Bito, L. Z., "Prostaglandins, Other Eicosanoids, and Their Derivatives as Potential Antiglaucoma Agents," Applied Pharmacology in the Medical Treatment of Glaucomas, Drance, S. M. and Neufield, A. H. eds., New York, Grune & Stratton, 1984, pp. 477–505.
Nilsson, et al., Invest. Ophthalmol. Vis. Sci. 28 (suppl), 284 (1987).
Bito, L. Z., "Prostaglandins, Old Concepts and New Perspectives," Arch. Ophthalmol. 105, 1036 (1987).
Siebold, et al., "Esterified prostaglandin shows 'potent' promise," Prodrug 5, 3 (1989).

*Primary Examiner*—Robert Gerstl
*Attorney, Agent, or Firm*—Robert J. Baran; Martin A. Voet; James M. Hoch

[57] ABSTRACT

The present invention relates to cyclopentane heptenylnitro and heptanylnitro-2-aliphatic or arylaliphatic derivatives. In particular, heptenylnitrate and heptanylnitrate 2-aliphatic or arylaliphatic derivatives, substituted at the 3 and/or 5 position of the cyclopentane ring with radicals selected from the group consisting of hydroxy, alkylcarboxy and mixtures thereof, are disclosed. These compounds are useful as ocular hypotensives.

24 Claims, No Drawings

CYCLOPENTANE HEPTENYLNITRO AND HEPTANYLNITRO-2-ALIPHATIC OR ARYL ALIPHATIC DERIVATIVES AND HOMOLOGUES

FIELD OF THE INVENTION

The present invention relates to cyclopentane heptenylnitro and heptanylnitro-2-aliphatic or arylaliphatic derivatives and homologues. In particular, heptenylnitro and heptanylnitro 2-aliphatic or arylaliphatic derivatives, substituted at the 3 and/or 5 position of the cyclopentane ring with radicals selected from the group consisting of hydroxy, alkylcarboxy and mixtures thereof, are disclosed. These compounds are useful as ocular hypotensives.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its eitology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical $\beta$-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are ideally suited for the long-term medical management of glaucoma. (See, for example, Starr M. S. *Exp. Eye Res.* 1971, 11, pp. 170–177; Bito, L. Z. *Biological Protection with Prostaglandins* Cohen, M. M., ed., Boca Raton, Fla., CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostaglandins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

In the U.S. Pat. No. 4,599,353 certain prostaglandins, in particular $PGE_2$ and $PGF_{2\alpha}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uveoscleral outflow [Nilsson et al., *Invest. Ophthalmol. Vis. Sci.* 28(suppl), 284 (1987)].

The isopropyl ester of $PGF_{2\alpha}$ has been shown to have significantly greater hypotensive potency than the parent compound, which was attributed to its more effective penetration through the cornea. In 1987 this compound was described as "the most potent ocular hypotensive agent ever reported." [See, for example, Bito, L. Z., *Arch. Ophthalmol.* 105, 1036 (1987), and Siebold et al., *Prodrug* 5, 3 (1989)].

Whereas prostaglandins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of prostaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of co-pending U.S. patent applications assigned to Allergan, Inc. prostaglandin esters with increased ocular hypotensive activity accompanied with no or substantially reduced side-effects are disclosed. The co-pending U.S. Ser. No. 386,835 (filed Jul. 27, 1989), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 357,394 (filed May 25, 1989). Similarly, 11,15- 9,15- and 9,11-diesters of prostaglandins, for example 11,15-dipivaloyl $PGF_{2\alpha}$ are known to have ocular hypotensive activity. See the co-pending patent applications U.S. Ser. No. 385,645 filed Jul. 27, 1990, now U.S. Pat. No. 4,494,274; U.S. Ser. No. 584,370 which is a continuation of U.S. Ser. Nos. 386,312, and 585,284, now U.S. Pat. No. 5,034,413 which is a continuation of U.S. Ser. No. 386,834, where the parent applications were filed on Jul. 27, 1989. The disclosures of these patent applications are hereby expressly incorporated by reference.

SUMMARY OF THE INVENTION

We have found that certain cyclopentane heptenylnitro and heptanylnitro-2-aliphatic or arylaliphatic derivatives are potent ocular hypotensive agents. Moreover, when these compounds are used to treat glaucoma, they cause no or significantly lower ocular surface hyperemia than many other compounds having hypotensive activity.

The present invention relates to methods of treating ocular hypertension which comprises administering an effective amount of a cyclopentane heptenylnitro and heptanylnitro-2-aliphatic or arylaliphatic derivatives represented by the formula I

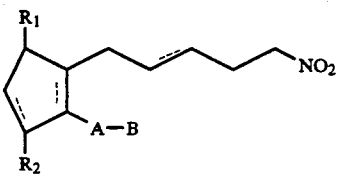

wherein A is an alkylene or alkenylene radical having from two to seven carbon atoms, e.g. about four to seven carbon atoms, which radical may be substituted with one or more hydroxy, oxo, alkyloxy or alkylcarboxy groups, and B is a methyl radical or a cycloalkyl radical having from three to seven carbon atoms, e.g. about five to six carbon atoms, or an aryl radical, selected from the group consisting of hydrocarbyl aryl and heteroaryl radicals wherein the heteroatom is selected from the group consisting of nitrogen, oxygen and sulfur atoms, and $R_1$ and $R_2$ are independently selected from the group consisting of hydryl, hydroxy, or alkyl carboxy radicals, i.e. ester derivatives of hydroxy as defined below. For example, A may be a straight chain alkylene radical, e.g. heptylene, or alkenylene radical, e.g. 3-hydroxy-1-heptylenyl, and B may be selected from the group consisting of methyl, cyclopentyl, cyclohexyl, phenyl, thienyl, furanyl, pyridyl, etc. B may also be substituted by radicals selected from the group consisting of halo, e.g. fluoro, chloro, etc., nitro, amino, thiol, hydroxy, alkyloxy, alkylcarboxy, etc. Preferably, B is methyl.

More preferably the method of the present invention comprises administering a cyclopentane heptenylnitro and heptanylnitro-2-aliphatic or arylaliphatic derivatives represented by the formula II

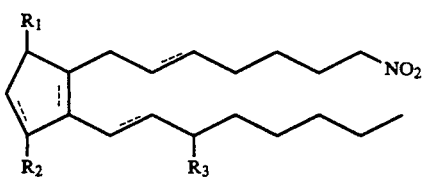

wherein either the α or ω chain may be unsaturated, the dashed bonds represent a single bond or a double bond which can be in the cis or trans configuration and $R_3$ is =O, —OH or —O(CO) $R_6$; wherein $R_6$ is a saturated or unsaturated acyclic hydrocarbon group having from 1 to about 20 carbon atoms, or —(CH$_2$)$_m$R$_7$ wherein m is 0-10, and $R_7$ is an aliphatic ring from about 3 to about 7 carbon atoms, or an aryl or heteroaryl ring, as defined above; or a pharmaceutically acceptable salt thereof. Preferably the derivative used in the above method of treatment is a compound of formula (III).

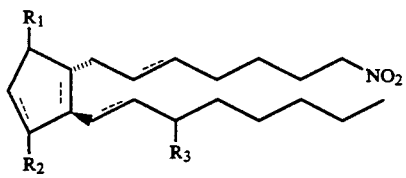

wherein hatched lines indicate α configuration, solid triangles are used to indicate β configuration and the dashed bonds represent a single bond or a double bond which can be in the cis or trans configuration and $R_1$ and $R_2$ are —OH or —O(CO)$R_6$ or hydrl (i.e. —H).

In another aspect, the present invention relates to a method of treating ocular hypertension which comprises administering to a subject a pharmaceutical composition comprising a therapeutically effective amount of a compound of formula (IV)

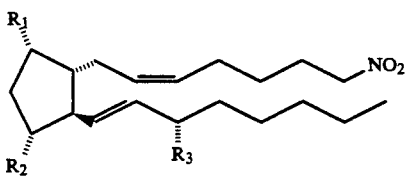

wherein the symbols and substituents are as defined above, in combination with a pharmaceutical carrier.

In a further aspect, the present invention relates to pharmaceutical compositions comprising a therapeutically effective amount of a compound of formulae (I), (II), (III), or (IV) wherein the symbols have the above meanings, or a pharmaceutically acceptable salt thereof in admixture with a non-toxic, pharmaceutically acceptable liquid vehicle.

In a still further aspect, the present invention relates to of the above formulae, wherein the substituents and symbols are as defined hereinabove, or a pharmaceutically acceptable salt of such compounds.

DETAILED DESCRIPTION OF THE INVENTION

The present invention relates to the use of cyclopentane heptenylnitro and heptanylnitro-2-ali-phatic or arylaliphatic derivatives as ocular hypotensives. These therapeutic agents are represented by compounds having the formula I,

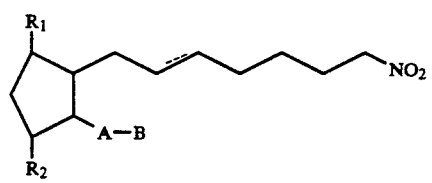

as defined above. Cyclopentane heptenylnitro and heptanylnitro-2-aliphatic or arylaliphatic derivatives used in accordance with the present invention are encompassed by the following structural formula (II)

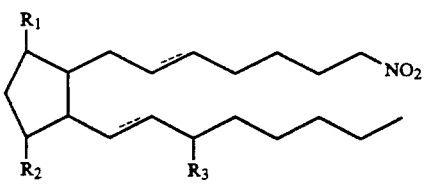

wherein the substituents and symbols are as hereinabove defined. More preferably the derivatives are represented by formula (III).

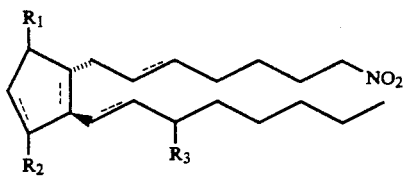

wherein the substituents and symbols are as defined above. More preferably, the derivatives utilized in the present invention are compounds represented by the formula (IV)

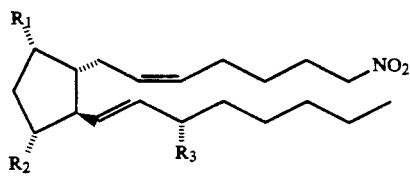

wherein the substituents and the symbols are as defined above.

Most preferably the present invention utilizes the novel derivatives of the formulae (V),

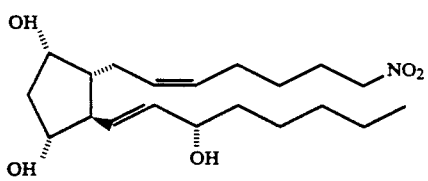

Formula V and its esters, i.e. the —O(CO)$R_6$ esters defined above.

In all of the above formulae, as well as in those provided hereinafter, the dotted lines on bonds between carbons 5 and 6 (C-5), between carbons 13 and 14 (C-13), between carbons 8 and 12 (C-8), and between carbons 10 and 11 (C-10) indicate a single or a double bond which can be in the cis or trans configuration. If two solid lines are used that indicates a specific configuration for that double bond. Hatched lines at positions C-9, C-11 and C-15 indicate the α configuration. If one were to draw the β configuration, a solid triangular line would be used.

In the compounds used in accordance with the present invention, compounds having the C-9 or C-11 or C-15 substituents in the α or β configuration are contemplated. As hereinabove mentioned, in all formulas provided herein broken line attachments to the cyclopentane ring indicate substituents in the α configuration. Thickened solid line attachments to the cyclopentane ring indicate substituents in the β configuration. Also, the broken line attachment of the hydroxyl group or other substituent to the C-11 and C-15 carbon atoms signifies the α configuration.

For the purpose of this invention, unless further limited, the term "aliphatic" means linear and branched alkylene and alkenylene radicals, the terms "alkylene" and "alkenylene" mean divalent radicals derived from alkanes and alkenes, respectively. The term "alkyl" refers to alkyl groups having from one to ten carbon atoms, the term "cycloalkyl" refers to cycloalkyl groups having from three to seven carbon atoms, the term "aryl" refers to aryl groups having from four to ten carbon atoms. The term "saturated or unsaturated acyclic hydrocarbon group" is used to refer to straight or branched chain, saturated or unsaturated hydrocarbon groups having from one to about six, preferably one to about four carbon atoms. Such groups include alkyl, alkenyl and alkynyl groups of appropriate lengths, and preferably are alkyl, e.g. methyl, ethyl, propyl, butyl, pentyl, or hexyl, or an isomeric form thereof.

The definition of $R_6$ may include a cyclic component, —$(CH_2)_m R_7$, wherein n is 0–10, $R_7$ is an aliphatic ring from about 3 to about 7 carbon atoms, or an aromatic or heteroaromatic ring. The "aliphatic ring" may be saturated or unsaturated, and preferably is a saturated ring having 3 to 7 carbon atoms, inclusive. As an aromatic ring, $R_7$ preferably is phenyl, and the heteroaromatic rings have oxygen, nitrogen or sulfur as a heteroatom, i.e., $R_7$ may be thienyl, furanyl, pyridyl, etc. Preferably m is 0–4.

A preferred representative of the compounds within the scope of the present invention is a compound of formula V, cyclopentane heptenylnitro, 5-cis-2-(3-α hydroxy-1-trans-octenyl)-3,5-dihydroxy, [1α, 2β, 3α, 5α].

A pharmaceutically acceptable salt is any salt which retains the activity of the parent compound and does not impart any deleterious or undesirable effect on the subject to whom it is administered and in the context in which it is administered. Such salts are those formed with pharmaceutically acceptable cations, e.g., alkali metals, alkali earth metals, etc.

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edentate disodium, (sodium EDTA) although other chelating agents may also be used in place of or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material and generally contain between about 0.5 and about 15 ml solution. One package may contain one or more unit doses.

Especially preservative-free solutions are often formulated in non-resealable containers containing up to about ten, preferably up to about five unit doses, where a typical unit dose is from one to about 8 drops, preferably one to about 3 drops. The volume of one drop usually is about 20–35 μl.

EXAMPLE 1

Cyclopentane heptenylnitrate methyl, 5-cis-2-(3-α hydroxy-1-trans-octenyl)-3,5-dihydroxy, [1α, 2β, 3α, 5α]

The methyl ester of the prostaglandin $PGF_{2\alpha}$ (prepared from $PGF_{2\alpha}$ and diazomethane, 2.29 g, 6.22 mmol), was dissolved in $CH_2Cl_2$ (6.2 ml). 1,2-Dihydro-3H-pyran (THP) (5.7 ml, 62 mmol) was added followed by pyridinium tosylate (156 mg, 0.62 mmol). The reaction was stirred at 25° C. for 19 hours (h) and quenched with 10% citric acid. After being extracted into ethyl acetate, the crude product solution was washed with saturated sodium bicarbonate and brine, dried over magnesium sulfate and concentrated to give the crude 9,11,15-tris (THP) ether of the $PGF_{2\alpha}$ methyl ester.

A 1.0M solution of diisobutylaluminum hydride in methylene chloride (7.8 ml, 7.8 mmol) was added at −78° C. to the crude product (1.6 g, 2.6 mmol) obtained above. The resulting solution was stirred at −78° C. for 4 h and worked up by the addition of a saturated solution of Rochelle salt. The mixture was extracted three times with ethyl acetate. The organic extract was washed with brine and dried over magnesium sulfate. The solvent was evaporated to give 1.47 g of crude product which was chromatographed over silica gel (40–50% ethyl acetate in hexane) to give 1.2 g (78% yield) of pure 9,11,15-tris (THP) ether cyclopentane heptenol, 5-cis-2-(3α hydroxy-1-trans-octenyl)-3,5-dihydroxy, [1α, 2β, 3α, 5α] (hereinafter the "Alcohol Intermediate").

The tris (THP) ether from above (500 mg, 0.84 mmol) and triethylamine (180 ul, 1.,26 mmol) were dissolved in methylene chloride (1.6 ml) and cooled to 0° C. To the above solution was added dropwise over ca 5 min. methanesulfonyl chloride (70 ul, 0.90 mmol). The solution was stirred at 0° C. for 2 h and worked up by addition of 10% citric acid. The crude reaction mixture was extracted with methylene chloride and the extracts were washed with saturated sodium bicarbonate and brine. The organic phase was dried over anhydrous magnesium sulfate and concentrated to give 543 mg of the 1-mesylate.

The crude mesylate was dissolved in acetone (1.6 ml) and sodium iodide (303 mg, 2.0 mmol) and calcium carbonate (81 mg, 0.81 mmol) were added. The suspension was stirred over the weekend and diluted with ethyl acetate. The crude product was washed successively with water and brine and dried over anhydrous magnesium sulfate. The solvents were removed under reduced pressure to give 522 mg yellow oil. Purification was achieved by column chromatography on silica gel, first with 20% ethyl acetate in hexane ($R_f$ 0.18) and then with 40% ethyl acetate in hexane ($R_f$ 0.6) to give 220 mg pure iodide.

Sodium nitrite (15 mg, 0.18 mmol) was added to a solution of the iodide (62 mg, 0.088 mmol) in dimethyl sulfoxide (DMSO) (0.2 ml).. The reaction was stirred at room temperature for a total of 72 h with addition of sodium nitrite (2–15 mg portions) at regular intervals. The reaction was worked up by the addition of water followed by extracted with ethyl acetate. The organic extract was washed with water and brine, dried (anhydrous magnesium sulfate) and concentrated to give the crude product which was purified with column chromatography (silica gel, 40% ethyl acetate in hexane $R_f$ 0.26) to give 25 mg (46% yield) of tris (THP) ether of the named compound and 8 g of the Alcohol Intermediate.

The tris (THP) ether of the named compound from above and pyridinium tosylate (13 mg) were dissolved in methanol (2 ml) and heated to 50° C. for 2.5 h. The methanol was evaporated and the residue was partitioned between ethyl acetate and water. The aqueous phase was extracted and the residue was partitioned between ethyl acetate and water. The aqueous phase was extracted with 2 portions of ethyl acetate and the combined organic extracts were washed with 10% citric acid, saturated sodium bicarbonate and brine. After drying and removal of solvent, the crude product was submitted to column chromatography (silica gel, ethyl acetate, $R_f 0.26$) to give 7.5 mg (58% yield) of the pure named compound.

EXAMPLE 2

Intraocular Pressure

Intraocular pressure was measured by pneumatonometry in male and female Beagle dogs (10–15 kg). Studies were performed in conscious animals trained to accept pneumatonometry. Drugs were administered topically to one eye in a 25 ul volume drop, the contralateral eye received vehicle as a control. Statistical analysis was by Student's paired t test. See Table I below for the results obtained.

TABLE 1

EFFECT ON INTRAOCULAR PRESSURE (mm Hg) CHANGES AT PREDETERMINED TIMES (HR) AFTER PG ADMINISTRATION

| COMPOUND (DOSE %) OF EXAMPLE 1 | AT PREDETERMINED TIMES (HR) AFTER PG ADMINISTRATION | | | | |
|---|---|---|---|---|---|
| | 1 | 2 | 3 | 4 | 6 |
| 0.01% | −1.4 | −2.3 | −1.4 | −1.5 | +1.0 |
| 0.1% | +0.6 | −3.8 | −4.8 | −1.7 | −0.6 |

The foregoing description details specific methods and compositions that can be employed to practice the present invention, and represents the best mode contemplated. However, it is apparent from one of ordinary skill in the art that further compounds with the desired pharmacological properties can be prepared in an analogous manner, i.e. compounds of the formula VI

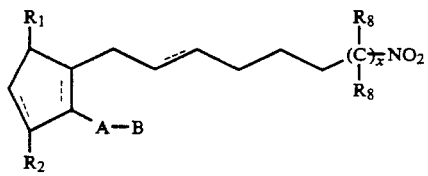

wherein X is an integer of from 1 to 3 and $R_8$ is selected from the group consisting of hydrogen and $C_1$–$C_3$ alkyl, e.g. methyl. Furthermore, the disclosed compounds can also be obtained from different starting compounds via different chemical reactions. Similarly, different pharmaceutical compositions may be prepared and used with substantially the same results. Thus, however detailed the foregoing may appear in text, it should not be construed as limiting the overall scope hereof; rather, the ambit of the present invention is to be governed only by the lawful construction of the appended claims.

I claim:

1. A method of treating ocular hypertension which comprises administering an effective amount of a compound represented by the formula VI

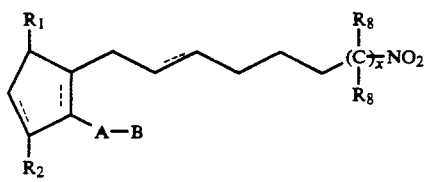

wherein X is an integer from one to three and $R_8$ is selected from the group consisting of hydrogen and $C_1$–$C_3$ alkyl, the dashed bonds represent a single bond or a double bond which can be in the cis or trans configuration, A is an alkylene or alkenylene radical having from two to seven carbon atoms, which radical may be substituted with one or more hydroxy, oxo, alkyloxy or alkylcarboxy groups containing 1 to 10 carbon atoms in the alkyl moieties, B is a methyl radical or a cycloalkyl radical having from three to seven carbon atoms, or an aryl radical selected from the group consisting of aryl and monoheteroaryl radicals having from 4 to 10 carbon atoms wherein the heteroatom is selected from the group consisting of nitrogen, oxygen and sulfur atoms, any of the groups defining B may be substituted by radicals from the group consisting of halo, nitro, amino, thiol, hydroxy, alkyloxy and alkylcarboxy containing 1 to 10 carbon atoms in the alkyl moieties, and $R_1$ and $R_2$ are independently selected from the group consisting of hydryl, hydroxy and 1–20 carbon alkyl ester derivatives thereof, or a pharmaceutically acceptable salt thereof.

2. The method of claim 1 wherein said derivative is represented by the formula II

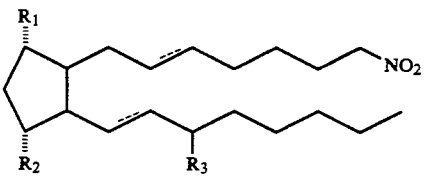

wherein either the $\alpha$ or $\omega$ chain may be unsaturated, and $R_3$ is =O, —OH or —O(CO)$R_6$; wherein $R_6$ is a saturated or unsaturated acyclic hydrocarbon group having from 1 to 20 carbon atoms, or —(CH$_2$)$_m$R$_7$ wherein m is 0–10, and $R_7$ is an aliphatic ring from about 3 to 7 carbon atoms, or a hydrocarbyl aryl or heteroaryl ring, as defined in claim 1; or a pharmaceutically acceptable salt thereof.

3. The method of claim 2 wherein the derivative is a compound of formula (III)

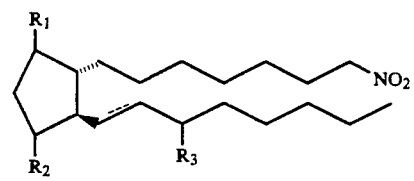

wherein hatched lines indicate $\alpha$ configuration, solid triangles are used to indicate $\beta$ configuration; $R_1$ and $R_2$ are —OH or —O(CO)$R_6$ or hydryl.

4. The method of claim 3 wherein said derivative is a compound of formula (IV)

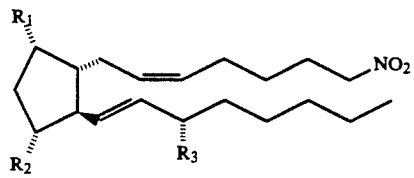

5. The method of claim 4 wherein said derivative is a compound selected from the group of compounds represented by the formula V:

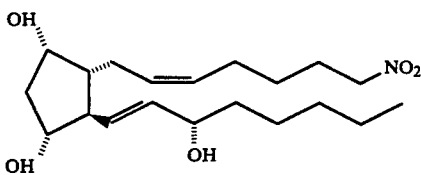

and their esters, wherein one or more of the hydroxyl groups may be replaced with —O(CO)R$_6$, where R$_6$ is as defined in claim 2.

6. The method of claim 1 wherein A is a straight chain alkylene radical or alkenylene radical and B is selected from the group consisting of methyl, cyclopentyl, cyclohexyl, phenyl, thienyl, furanyl, and pyridyl.

7. The method of claim 6 wherein A is 3-hydroxy-1-heptenylene and B is methyl.

8. The method of claim 1 wherein said derivative is cyclopentane heptenylnitrate, 5-cis-2-(3-αhydroxy-1-transoctenyl)-3,5-dihydroxy [1α,2β,3α,5α].

9. A pharmaceutical composition for treating ocular hypertension which comprises an effective amount of a compound represented by the formula VI

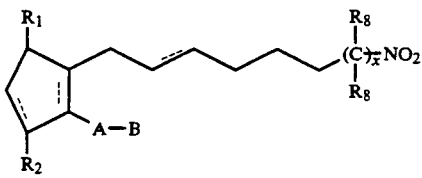

wherein X is an integer from one to three and R$_8$ is selected from the group consisting of hydrogen and C$_1$–C$_3$ alkyl, the dashed bonds represent a single bond or a double bond which can be in the cis or trans configuration, A is an alkylene or alkenylene radical having from two to seven carbon atoms, which radical may be substituted with one or more hydroxy, oxo, alkyloxy or alkylcarboxy groups containing 1 to 10 carbon atoms in the alkyl moieties, B is a methyl radical or a cycloalkyl radical having from three to seven carbon atoms, or an aryl radical selected from the group consisting of aryl and monoheteroaryl radicals having from 4 to 10 carbon atoms wherein the heteroatom is selected from the group consisting of nitrogen, oxygen and sulfur atoms, any of the groups defining B may be substituted by radicals from the group consisting of halo, nitro, amino, thiol, hydroxy, alkyloxy and alkylcarboxy containing 1 to 10 carbon atoms in the alkyl moieties, and R$_1$ and R$_2$ are independently selected from the group consisting of hydryl, hydroxy and 1–20 carbon alkyl ester derivatives thereof, or a pharmaceutically acceptable salt thereof in connection with an ophthalmically-acceptable vehicle.

10. The composition of claim 9 wherein said derivative is represented by the formula II

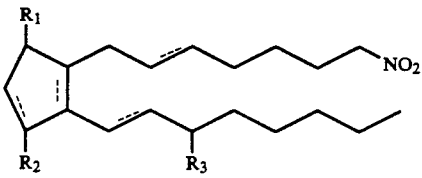

wherein either the α or ω chain may be unsaturated, and R$_3$ is =O, —OH or —O(CO)R$_6$; wherein R$_6$ is a saturated or unsaturated acyclic hydrocarbon group having from 1 to 20 carbon atoms, or —(CH$_2$)$_m$R$_7$ wherein m is 0–10, and R$_7$ is an aliphatic ring from 3 to 7 carbon atoms, or a hydrocarbyl aryl or heteroaryl ring, as defined in claim 1; or a pharmaceutically acceptable salt thereof.

11. The composition of claim 10 wherein the derivative is a compound of formula (III)

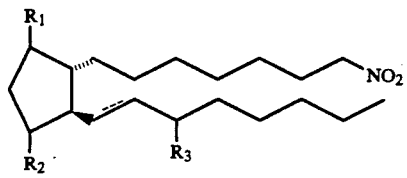

wherein hatched lines indicate α configuration, solid triangles are used to indicate β configuration; R$_1$ and R$_2$ are —OH or —O(CO)R$_6$ or hydryl.

12. The composition of claim 11 wherein said derivative is a compound of formula (IV)

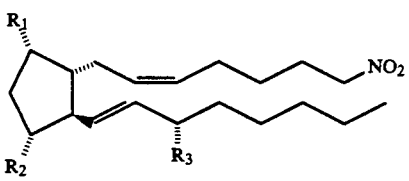

13. The composition of claim 12 wherein said derivative is a compound selected from the group of compounds represented by the formula V:

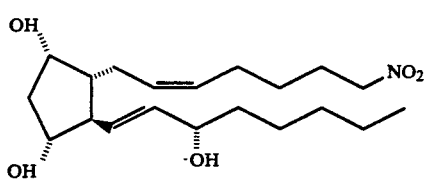

and their esters, wherein one or more of the hydroxyl groups may be replaced with —O(CO)R$_6$, where R$_6$ is as defined in claim 10.

14. The method of claim 9 wherein A is a straight chain alkylene radical or alkenylene radical and B is selected from the group consisting of methyl, cyclopentyl, cyclohexyl, phenyl, thienyl, furanyl, and pyridyl.

15. The composition of claim 14 wherein A is 3-hydroxy-1-heptenylene and B is methyl.

16. The composition of claim 9 wherein said derivative is cyclopentane heptenylnitrate, 5-cis-2-(3-αhydroxy-1-transoctenyl)-3,5-dihydroxy [1α,2β,3α,5α].

17. A compound, useful for treating ocular hypertension which comprises a compound represented by the formula VI

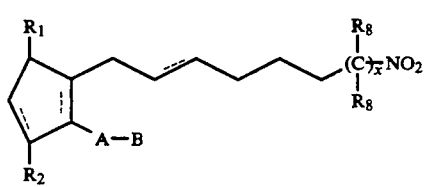

wherein X is an integer from one to three and $R_8$ is selected from the group consisting of hydrogen and $C_1$-$C_3$ alkyl, the dashed bonds represent a single bond or a double bond which can be in the cis or trans configuration, A is an alkylene or alkenylene radical having from two to seven carbon atoms, which radical may be substituted with one or more hydroxy, oxo, alkyloxy or alkylcarboxy groups containing 1 to 10 carbon atoms in the alkyl moieties, B is a methyl radical or a cycloalkyl radical having from three to seven carbon atoms, or an aryl radical selected from the group consisting of aryl and monoheteroaryl radicals having from 4 to 10 carbon atoms wherein the heteroatom is selected from the group consisting of nitrogen, oxygen and sulfur atoms, any of the groups defining B may be substituted by radicals from the group consisting of halo, nitro, amino, thiol, hydroxy, alkyloxy and alkylcarboxy containing 1 to 10 carbon atoms in the alkyl moieties, and $R_1$ and $R_2$ are independently selected from the group consisting of hydryl, hydroxy and 1-20 carbon alkyl ester derivatives thereof, or a pharmaceutically acceptable salt thereof.

18. The compound of claim 17 wherein said derivative is represented by the formula II

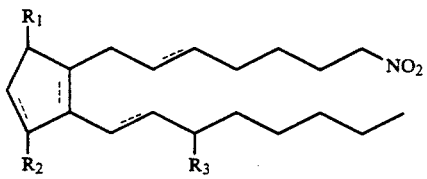

wherein either the $\alpha$ or $\omega$ chain may be unsaturated, and $R_3$ is =O, —OH or —O(CO)$R_6$; wherein $R_6$ is a saturated or unsaturated acyclic hydrocarbon group having from 1 to 20 carbon atoms, or —(CH$_2$)$_m$R$_7$ wherein m is 0-10, and $R_7$ is an aliphatic ring from 3 to 7 carbon atoms, or a hydrocarbyl aryl or heteroaryl ring, as defined in claim 1; or a pharmaceutically acceptable salt thereof.

19. The compound of claim 18 wherein the derivative is a compound of formula (III)

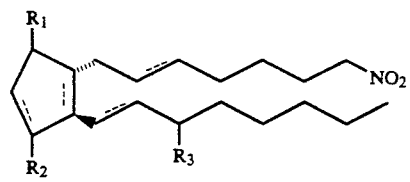

wherein hatched lines indicate $\alpha$ configuration, solid triangles are used to indicate $\beta$ configuration; $R_1$ and $R_2$ are —OH or —O(CO)$R_6$ or hydryl.

20. The compound of claim 19 wherein said derivative is a compound of formula (IV)

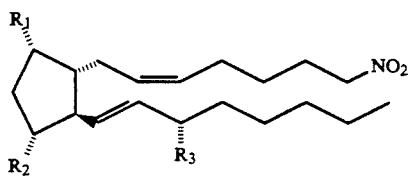

21. The compound of claim 17 wherein said derivative is a compound selected from the group of compounds represented by the formula V:

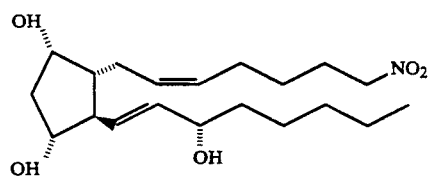

and their esters, wherein one or more of the hydroxyl groups may be replaced with —O(CO)$R_6$, where $R_6$ is as defined in claim 18.

22. The method of claim 17 wherein A is a straight chain alkylene radical or alkenylene radical and B is selected from the group consisting of methyl, cyclopentyl, cyclohexyl, phenyl, thienyl, furanyl, and pyridyl.

23. The compound of claim 22 wherein A is 3-hydroxy-1-heptenylene and B is methyl.

24. The compound of claim 17 wherein said derivative is cyclopentane heptenylnitrate, 5-cis-2-(3-αhydroxy-1-transoctenyl)-3,5-dihydroxy [1α,2β,3α,5α].

* * * * *

UNITED STATES PATENT AND TRADEMARK OFFICE
CERTIFICATE OF CORRECTION

PATENT NO. : 5,328,933
DATED : July 12, 1994
INVENTOR(S) : Ming Fai Chan

It is certified that error appears in the above-indentified patent and that said Letters Patent is hereby corrected as shown below:

Column 4, lines 56-64; delete

" 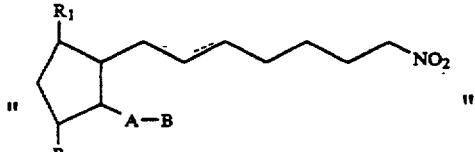 "

and insert in place thereof

-- 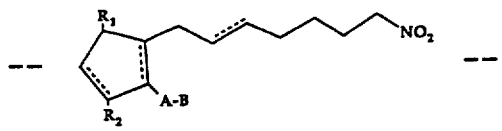 --

Column 5, lines 1-9; delete

" 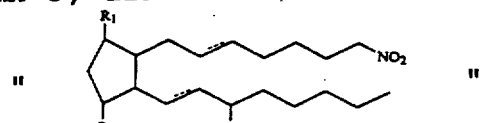 "

and insert in place thereof

-- 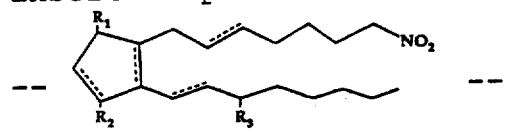 --

Column 10, claim 2, lines 22-30; delete

" 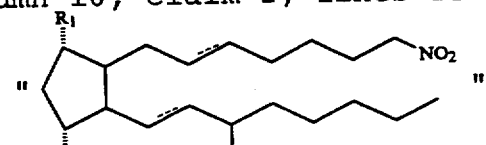 "

and insert in place thereof

-- 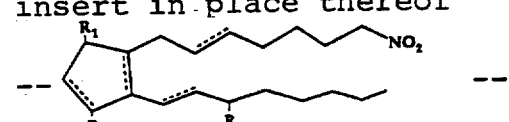 --

UNITED STATES PATENT AND TRADEMARK OFFICE
CERTIFICATE OF CORRECTION

PATENT NO. : 5,328,933
DATED : July 12, 1994
INVENTOR(S) : Ming Fai Chan

It is certified that error appears in the above-indentified patent and that said Letters Patent is hereby corrected as shown below:

Column 10, claim 3, lines 43-50; delete

" 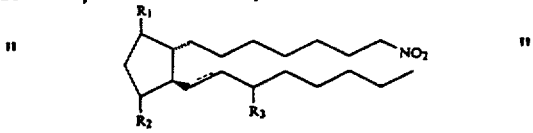 "

and insert in place thereof

-- 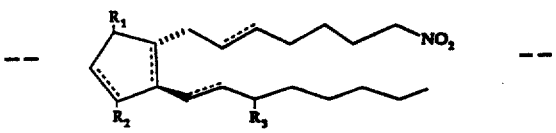 --

Column 12, claim 11, lines 8-15; delete

" 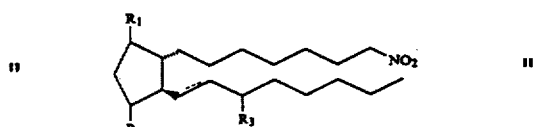 "

and insert in place thereof

-- 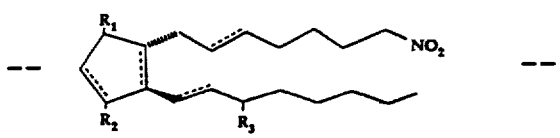 --

UNITED STATES PATENT AND TRADEMARK OFFICE
CERTIFICATE OF CORRECTION

PATENT NO. : 5,328,933
DATED : July 12, 1994
INVENTOR(S) : Ming F. Chan

It is certified that error appears in the above-indentified patent and that said Letters Patent is hereby corrected as shown below:

Column 4, line 15; delete "hydrl" and insert in place thereof --hydryl--

Column 4, line 43; after "to" insert --compounds--

Column 12, claim 14, line 47; delete "method" and insert in place thereof --composition--

Column 14, claim 22, line 38; delete "method" and insert in place thereof --compound--

Signed and Sealed this

Thirteenth Day of December, 1994

Attest:

BRUCE LEHMAN

*Attesting Officer*  *Commissioner of Patents and Trademarks*